(12) United States Patent
Mosler

(10) Patent No.: US 9,161,846 B2
(45) Date of Patent: Oct. 20, 2015

(54) PROSTHETIC FOOT

(75) Inventor: Lüder Mosler, Duderstadt (DE)

(73) Assignee: OTTO BOCK HEALTHCARE GMBH, Duderstadt (DE)

( * ) Notice: Subject to any disclaimer, the term of this patent is extended or adjusted under 35 U.S.C. 154(b) by 0 days.

(21) Appl. No.: 13/881,424

(22) PCT Filed: Oct. 25, 2011

(86) PCT No.: PCT/DE2011/001941
§ 371 (c)(1),
(2), (4) Date: Apr. 25, 2013

(87) PCT Pub. No.: WO2012/062279
PCT Pub. Date: May 18, 2012

(65) Prior Publication Data
US 2013/0218298 A1   Aug. 22, 2013

(30) Foreign Application Priority Data

Oct. 25, 2010  (DE) .......................... 10 2010 049 257
Nov. 8, 2010   (DE) .......................... 10 2010 050 493

(51) Int. Cl.
*A61F 2/66* (2006.01)
*A61F 2/50* (2006.01)

(52) U.S. Cl.
CPC ........... *A61F 2/66* (2013.01); *A61F 2002/5006* (2013.01); *A61F 2002/5007* (2013.01); *A61F 2002/6657* (2013.01); *A61F 2002/6678* (2013.01)

(58) Field of Classification Search
CPC ............. A61F 2/66; A61F 2002/6657; A61F 2002/6664

USPC ....................................... 623/47–56
See application file for complete search history.

(56) References Cited

U.S. PATENT DOCUMENTS

| 5,944,760 | A | 8/1999 | Christensen |
| 6,099,572 | A * | 8/2000 | Mosler et al. ................... 623/53 |
| 2002/0013628 | A1 | 1/2002 | Harris |
| 2002/0087216 | A1 | 7/2002 | Atkinson et al. |
| 2008/0167731 | A1 | 7/2008 | Christensen et al. |
| 2009/0012630 | A1 | 1/2009 | Mosler et al. |
| 2009/0306792 | A1 | 12/2009 | Lecomte et al. |
| 2010/0023135 | A1 | 1/2010 | Rubie et al. |
| 2010/0042228 | A1 | 2/2010 | Doddroe et al. |
| 2012/0271434 | A1 * | 10/2012 | Friesen et al. ................... 623/55 |

FOREIGN PATENT DOCUMENTS

DE  102006004132 A1  8/2007
WO     2004032809 A1  4/2004

OTHER PUBLICATIONS

PCT International Search Report for International Patent Application No. PCT/DE2011/001941, mailed May 14, 2012.

* cited by examiner

*Primary Examiner* — Bruce E Snow
(74) *Attorney, Agent, or Firm* — Holland & Hart

(57) ABSTRACT

A prosthetic foot with a base spring with a forefoot area and a heel area, a connecting means arranged above the base spring and used to fasten the prosthetic foot to a prosthesis, and a frontal support, at the upper end of which the connecting means is arranged and which, at its lower end, is secured on a torsion element that can twist about the longitudinal axis of the prosthetic foot. The torsion element is designed as a leaf spring arrangement secured to the base spring at one end in the heel area or in the forefoot area.

19 Claims, 5 Drawing Sheets

PROSTHETIC FOOT

TECHNICAL FIELD

The invention relates to a prosthetic foot with a base spring with a forefoot region and a heel region, a termination apparatus, arranged above the base spring, for affixing the prosthetic foot to a prosthesis and a frontal support, at the upper end of which the connection apparatus is arranged and the lower end of which is secured to a torsion element which can be twisted about the prosthesis longitudinal axis. The invention likewise relates to a prosthetic foot with a base spring with a forefoot region and a heel region, and a connection apparatus, arranged above the base spring, for affixing the prosthetic foot to a prosthesis.

BACKGROUND

DE 10 2006 004 132 A1 describes an artificial foot with an elastic sole structure, extending from a heel region to a toe region, with a longitudinal axis, a connection to a below-knee part, an upwardly extending upper support structure and an elastic connection element arranged between the upper support structure and the sole structure. The upper support structure is, in the longitudinal direction, connected to the sole structure approximately in the approximately in the center of the foot by means of a coupling arrangement, which allows a relative tilt movement between the sole structure and the support structure. Here, the distance between the support structure and the sole structure in the center of the coupling arrangement remains constant, at least when loaded by weight when the patients are standing. The joint arrangement consists of an elastic polymer cylinder, which supports itself on the sole structure with a lower end face and on the lower side of the support structure with an upper end face. A pin arrangement complements the polymer cylinder and has spherical heads on both of its ends, which spherical heads support themselves firstly on the sole structure and secondly on the support structure and increase the stability of the connection. It is likewise possible for the joint arrangement in the form of a spherical cap to be formed with a correspondingly interacting ball socket in order thus to establish the tiltable connection between the support structure and the sole structure.

The artificial foot in accordance with the prior art renders it possible to improve the rollover action during walking; moreover, well defined statics in standing are present as a result of a forwardly displaced force transmission point. However, only small restoration forces can be realized by the elastic polymer cylinder, and so the spring properties of the artificial foot during walking have to be realized only by the sole structure. Moreover, as a result of the polymer cylinder, use is made of components susceptible to wear-and-tear, which is detrimental to the precision of the force transmission.

SUMMARY

It is an object of the present invention to provide a prosthetic foot which offers improved options for adjusting the rollover behavior of the prosthetic foot and precise statics during standing, even in the case of variable conditions underfoot.

According to the invention, this object is achieved by a prosthetic foot with the features of the main claim or the coordinate claim. Advantageous embodiments and developments are listed in the dependent claims, the description and the figures.

The prosthetic foot according to the invention with a base spring with a forefoot region and a heel region, a connection apparatus, arranged above the base spring, for affixing the prosthetic foot to a prosthesis and a frontal support, at the upper end of which the connection apparatus is arranged and the lower end of which is secured to a torsion element which can be twisted about the prosthetic-foot longitudinal axis provides for the torsion element to be configured as a leaf spring apparatus, secured at one end either in the heel region or in the forefoot region. As a result of clamping the torsion element at one end in the heel region, it is possible for there also to be a bend about an axis extending transversely with respect to the longitudinal axis of the foot in addition to a twist about the longitudinal axis of the foot when the heel region is set down, such that the torsion element, in addition to the option of an angular compensation in the walking direction, also provides an additional spring element in order to enable the heel to be set down relatively softly. After the forefoot region is set down and while the prosthetic foot rolls over, the free, front end of the torsion element then rests against the base spring such that this results in stiffening by a parallel connection of the base spring and the torsion element. The prosthetic foot according to the invention renders it possible to convert the well-defined statics by means of the forwardly displaced force transmission point into a dynamic construction and in this case simultaneously ensure the standing stability, even in the case of changes underfoot or in the case of different shoes. The torsion element, which in general prevents a displaceability or deformability along the longitudinal extent of the prosthetic foot, is used to keep the resting point of the support structure on the sole structure precisely constant in space, without it being possible for the force transmission position to change due to wear-and-tear.

In an alternative embodiment of the invention, provision is made for the prosthetic foot to be equipped with a base spring with a forefoot region and a heel region, and a connection apparatus, arranged above the base spring, for affixing the prosthetic foot to a prosthesis, wherein the connection apparatus is secured to a torsion element which can be twisted about the prosthetic-foot longitudinal axis, which torsion element is configured as a leaf spring apparatus, secured at one end to the base spring in the heel region. The torsion element as a leaf spring is only secured in the heel region of the base spring, and so, when the heel is set down, the front end of the torsion element distances itself from the base spring and increases the distance in the front region of the torsion element from the base spring. Here, the connection apparatus is arranged in front of the point where the torsion element is affixed to the base spring such that the torsion element likewise has a resilient effect as well when the heel is set down. During the course of the further standing phase, the base spring lowers for complete contact on the ground. Subsequently, the torsion element is lowered further in the direction of the base spring until the front end of the torsion element rests on the upper side of the base spring. As the load on the forefoot increases, both the base spring and the torsion element bend together in the direction of the ground such that the base spring and the torsion element act together and are connected in parallel. Here, the torsion element rests on the upper side of the base spring and the forces acting on the rear end of the torsion element are transmitted on to the base spring in the attachment means, e.g. screws, by means of which the torsion element is affixed to the base spring. In order to prevent hard impact of the front part of the torsion element on the base spring, provision is made for a cushioning element, for example foam or the like. As a result of securing the torsion element at one end in the heel region, both twisting about the longitudinal axis of the foot and cushioning about an axis extending in the medial/lateral direction are possible, and so it is possible to achieve a simple adjustment of the base spring to uneven underfoot conditions as well when standing, i.e. during the standing phase.

In the case of one-ended linkage of the torsion element in the forefoot region, there is a parallel connection of the base spring and the torsion element when a heel is set down, and so a stable foot set-down is ensured. During the course of the rollover movement, the torsion element can, during increasing forefoot load, be bent open about an axis transverse to the longitudinal direction such that an additional spring is available for adjusting the elasticity of the prosthetic foot. The ability of the torsion element to twist changes differently during the standing phase, depending on the point of the linkage.

As a result of the one-ended linkage of the torsion element, the other end, which is not secured to the base spring, can distance itself from the base spring during a flexural load, i.e. increase the distance between the base spring and the torsion element, or else reduce said distance if, in the initial position, there is a displacement path in the direction of the base spring.

A clear space can be formed between the base spring and the torsion element in order firstly to enable a displacement in the direction of the base spring and secondly, in the case of a platform or cushioning between the base spring and the torsion element, to provide for an additional bend of the torsion element, even in the state where the torsion element rests against the platform or cushioning.

A buffer element can be arranged between the torsion element and the base spring in order to damp the impact of the torsion element on the base spring during the rollover or when setting down the foot. The buffer element can have a shape which allows twisting of the torsion element, even in the state where it rests against the base spring, for example a rounded shape or designed as a web, such that it is possible for the torsion element to tilt relative to the base spring. As an alternative to this, the contact area between the torsion element and the base spring can have a planar design such that no torsion is possible during the standing phase when the torsion element rests against the base spring. This provides greater stability of the prosthetic foot.

As a result of the configuration of the torsion element as a leaf spring apparatus, i.e. as a single part or multipart leaf spring, provision is made for the torsion element to be able to be twisted about an axis extending in the medial/lateral direction such that the individual spring elements, namely the torsion element and the base spring, become active in a staggered fashion.

The frontal support, which leads from the connection apparatus, for example a connection adapter, to the torsion element can likewise be configured as a spring or as a spring package in order to provide an additional spring component by means of which an adaptation to the respective prosthetic-foot user and the respective field of use or the preferences of the prosthetic-foot user can be set. The frontal support is preferably configured as a leaf spring or as a leaf spring package.

The frontal support can be configured in such a way that it can be twisted about a vertical axis such that, is the standing phase, there is a certain amount of resilience, even in the case of a rotational load about a vertical axis, such that, even in the case of complete contact of the prosthetic foot with the ground underfoot, a rotatability and resilience about a vertical axis are possible. As a result of this, the comfort of the behavior of the prosthetic foot during walking or standing can be increased for a prosthetic-foot user.

In the walking direction, the frontal support preferably ends in front of the connection apparatus, i.e. approximately in the region in which the force vector of the ground reaction force runs through the prosthetic foot during standing. The frontal support therefore ends approximately three to five centimeters from the connection apparatus in the anterior direction.

The frontal support can support itself on the base spring in a support region, which is situated in front of the connection apparatus in the walking direction. The support region can be equipped by the torsion element or by webs, cushions, dampers or the like below the torsion element or on the base spring. The frontal support can support itself on the base spring in the center of the base spring, wherein a central support is advantageous both in the longitudinal direction and in the transverse direction.

A heel spring, which, as an additional spring element, enables force to be taken up during the heel strike, can be arranged on the base spring. A damping element can be arranged between the base spring and the heel spring in order to convert the kinetic energy when the foot is set down into deformation energy or heat.

A damping element or a resilient element, which is supported on the base spring or on the torsion element in the heel region of the base spring, can be arranged on the connection apparatus or on the upper end of the frontal support. Such an embodiment is provided in particular if the torsion element is secured at one end in the heel region. As a result, there can be additional damping of the heel strike. The damping element can be configured as a fluid damper, in particular as a hydraulic damper or pneumatic damper, in order to be able to achieve simple adjustability of the degree of damping. Fluid dampers can be set separately both in the rebound travel and in the compression travel such that a variable compression behavior and rebound behavior of the connection apparatus or of the compression piston can be ensured. In addition to the better adjustability, the damper has the property of not building up any forces statically. Hence the foot can repeatedly adapt itself to the conditions underfoot or to the shoes when standing; all that act are the restoration forces of the relatively flexible torsion spring.

The damping element has at least one multi-axially movable joint, such that, in addition to pivoting about a medial/lateral axis during compression, there can, for example, also be a rotation about an anterior/posterior axis in order to be able also to allow twisting of the torsion element and hence tilting of the connection apparatus relative to the base spring. The multiaxial joint is preferably formed on a mount point on the connection apparatus or the base spring such that the damping element itself can perform a stable linear motion.

BRIEF DESCRIPTION OF THE DRAWINGS

In the following text, an exemplary embodiment of the invention will be explained in more detail on the basis of the attached figures. The same components are denoted by the same reference signs. In detail.

DETAILED DECSRIPTION

Figure 1:
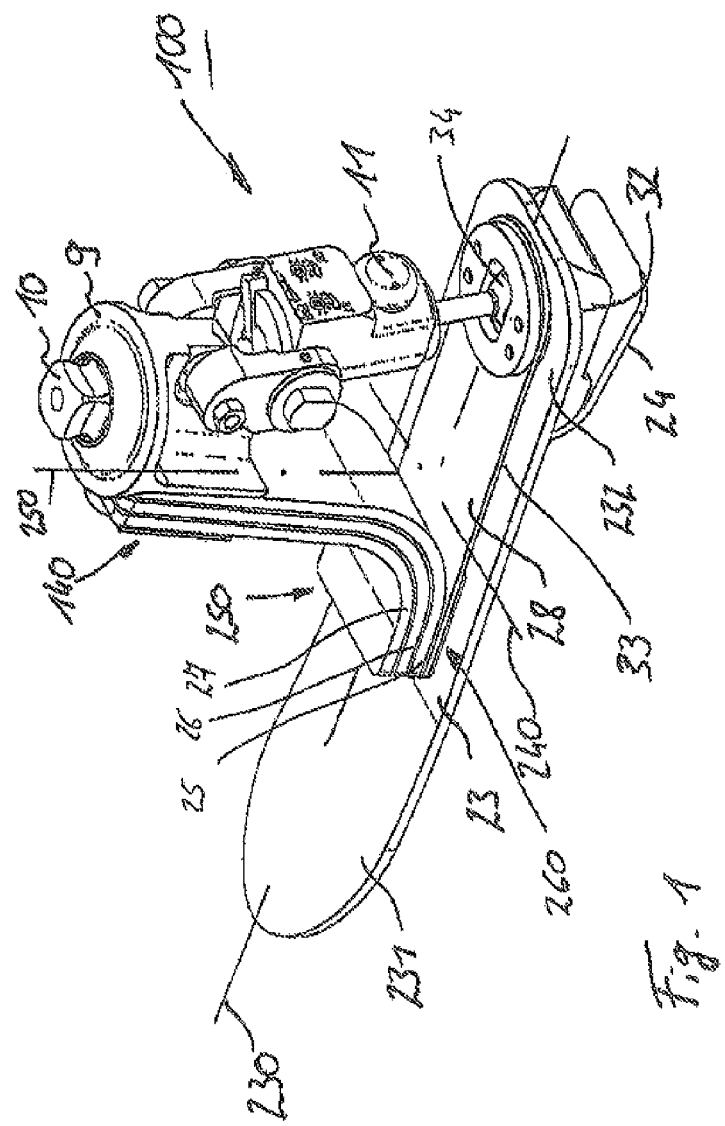
FIG. 1 shows a perspective overall view of a prosthetic foot.

FIG. 1 shows a prosthetic foot 100 in a perspective oblique plan view. The prosthetic foot 100 has a base spring 23 with a forefoot region 231 and a heel region 232. The base spring 23 is preferably manufactured from a fiber composite material, more particularly a carbon fiber component. The base spring 23 has an elongate configuration, wherein the prosthetic-foot longitudinal axis 230 extends in the longitudinal direction. The base spring 23 has a substantially straight design; a slight curvature is provided in the forefoot region 231 in order to facilitate a rollover action of the prosthetic foot 100.

A heel spring 24 is arranged on the base spring 23 in the heel region 232. The heel spring 24 is likewise made of a fiber composite material, more particularly of a carbon fiber material. The heel spring 24 can be affixed to the base spring 23 in an interchangeable fashion. A clear space which tapers off in the walking direction is provided between the heel spring 24 and the base spring 23, in which clear space a damping element 32 is arranged. This damping element can also be used to secure the heel spring 24 to the base spring 23.

A torsion element 28 in the form of a leaf spring is arranged on the upper side of the base spring 23. The torsion element 28 is secured in the heel region 232 of the base spring 23; the way in which it is secured will be explained on the basis of FIG. 2. The torsion element 28 is only affixed to the base spring 23 at one end; the front end of the torsion element 28 in the walking direction is not secured and can therefore be moved toward the base spring 23 and away from the base spring 23.

The front end of the torsion element 28 ends in a support region 260, which is arranged approximately in the center of the length of the base spring 23. The torsion element 240 can be twisted about the prosthetic-foot longitudinal axis 230; it can likewise be bent about a torsion axis 240 extending in the medial/lateral direction such that the front end of the torsion element 28 can be bent away from the upper side of the base spring 23. A clear space 33 is arranged between the torsion element 28 and the base spring 23, which clear space allows slight bending, even in the state where the front end of the torsion element 28 rests on the base spring 23.

A frontal support 25, 26, 27 in the form of a leaf spring package is affixed to the front end of the torsion element 28. Affixing can be brought about by adhesive bonding, screwing, laminating or the like. The lower end 250 of the frontal support 25, 26, 27 extends substantially parallel to the torsion element 28. From the point where it is affixed to the torsion element 28, at which the frontal support 25, 26, 27 is secured in a rigid fashion, the frontal support 25, 26, 27 extends upwardly in an arc in the direction of a connection apparatus; which has a proximal adapter 9 and an adjustment core 10. The upper end 140 of the frontal support 25, 26, 27 has a straight configuration and is affixed to the proximal adapter 9 as part of the connection apparatus; the distal end of the connection apparatus is formed by an adjustment core 10 and serves for securing it to a below-knee prosthesis. In the anterior direction, the frontal support 25, 26, 27 is affixed to the proximal adapter 9; in this case too, there is a substantially rigid connection to the frontal support 25, 26, 27.

A hydraulic damper 11, which is affixed to the proximal adapter 9 in a hinged fashion, is arranged on the side of the adjustment core 10 lying opposite to the frontal support 25, 26, 27. The pivot axis of the upper mount extends substantially parallel to the medial/lateral axis 240. At the lower end of the damper 11, provision is made for a mount in a multiaxial, movable joint 34—a partial ball-and-socket joint in the exemplary embodiment—by means of which it is possible to carry out both a pivot about a medial/lateral axis and a rotation about the prosthetic-foot longitudinal axis 230. As a result of the multiaxial mount in the lower joint 34 and the rotationally symmetric embodiment of the movable piston or the piston rod, it is also possible for a twist to be carried out about a vertical axis 250.

Figure 2:
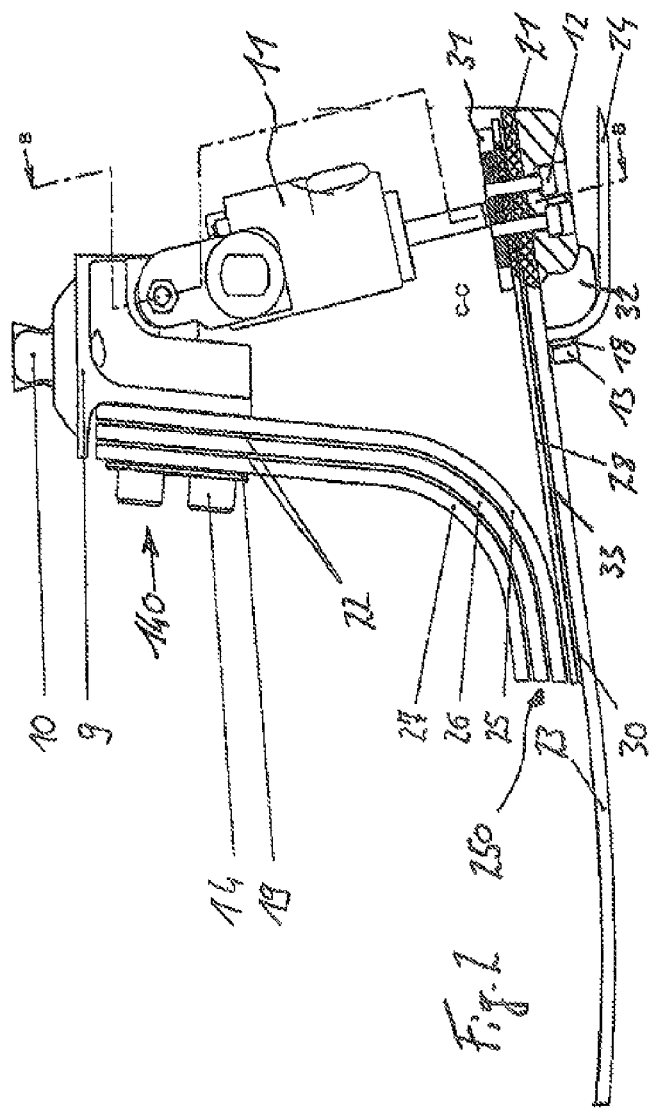
FIG. 2 shows a side view with a partly cut heel.
Figure 3:
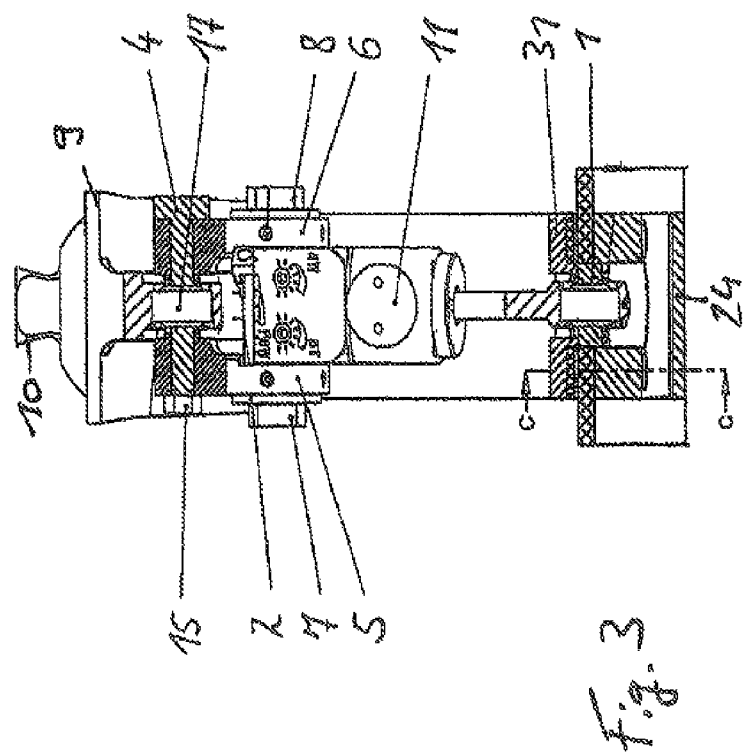
FIG. 3 shows a sectional illustration along B-B in FIG. 2.

FIG. 2 shows a side view of the prosthetic foot 100 in accordance with FIG. 1, with a detailed section along the line C-C in FIG. 3. In the side view in accordance with FIG. 2, it is initially possible to identify the substantially straight configuration of the base spring 23, which is slightly bent in the forefoot region 231. The torsion element 28 as a leaf spring rests in the resting region 260 above a buffer element 30 on the upper side of the base spring 23. The buffer element 30 extends over the whole width of the torsion element 28. Beyond the buffer element 30, a clear space 33 is provided between the torsion element and the base spring 23. The buffer element 30 preferably consists of a polymer, more particularly polyurethane.

It is likewise possible to gather from FIG. 2 that the lower end 250 of the frontal support 25, 26, 27 is affixed to the torsion element 28. In the illustrated exemplary embodiment, the frontal support 25, 26, 27 is made of three bent leaf spring elements 25, 26, 27. A clear space, which, for example, is ensured by spacer pieces 22 at the upper end 140 of the frontal support 25, 26, 27, is present between the individual leaf spring elements 25, 26, 27. Spacer pieces can likewise be arranged between the leaf spring elements 25, 26, 27 at the lower end 250 of the frontal support.

The upper end of the frontal support 25, 26, 27 is affixed to the proximal adapter 9 by means of screws 14. A pressure sheet 19 for uniformly transmitting the forces of the screws 14 onto the frontal leaf spring element 27 is provided between the screws 14 and the frontal leaf spring element 27.

The hydraulic damper 11 is affixed to the rear region of the proximal adapter 9. The lower end of the hydraulic damper 11 is secured to the heel region 232 of the base spring 23 via a heel arm 31. The heel arm is affixed to the base spring 23 by means of fillister screws 12. The fillister screws 12 pass through the base spring 23, a spacer 21 for ensuring the clear space 33 between the base spring 23 and the torsion element 28, and the torsion element 28 itself and are screwed into the heel arm 31. At the same time the damping element 32 is secured to the base spring 23 by means of the fillister screws 12. Fillister screws 13 and a pressure sheet 18 are used to affix the heel spring 24 to the damping element 32. As a result of the screwed connection, an interchangeable embodiment of the heel spring 24 can be realized, as a result of which there can be further adjustment to the respective prosthetic-foot user. Instead of a damping element 32, provision can also be made for an adapter plate, by means of which the heel spring 24 can be secured to the base spring 23. The adapter plate can serve as a support for the hydraulic damper 11. As a result of a rounded resting surface for the heel spring 24, it is possible to achieve increasing elevation of the resistance force since the effective length of the heel spring 24 reduces in the case of an increasing load.

FIG. 3 shows a section along the line B-B in FIG. 2. It is possible to identify a partly cut rear view of the prosthetic foot with the adjustment core 10 and the proximal adapter 9. Two holding arms 5, 6 are mounted on the proximal adapter 9 in a hinged fashion by means of a ball-and-socket joint 17 and a joint bolt 4 with a nut 15. The hydraulic damper 11 is affixed to the two holding arms 5, 6 via screws 7, 8. The heel arm 31 holds an adapter bolt 1, which is configured for a hinged mount of the hydraulic damper 11. The heel spring 24 forms the lower termination of the prosthetic foot 100.

If the prosthetic foot 100 in the illustrated embodiment is used, the heel spring 24 initially comes into contact with the ground. An elastic deformation occurs. Forces are transmitted to the base spring 23 by the screws 13 and the damping element 32. As a result of the one-ended clamping by the screws 12 of the torsion element 28, the front end lifts off the base spring 23 in the support region 260. The hydraulic damper 11 is compressed and the frontal support 25, 26, 27 is bent backward with the upper end 140. As a result of the front end of the torsion element 28 lifting and the capability thereof of twisting about the prosthetic-foot longitudinal axis 230, it is possible for a torsion and tilt movement to be carried out when the foot is set down such that the base spring 23 and the heel spring 24 can adapt to an uneven ground.

After the heel strike, the torsion element 28 and the leaf spring elements 25, 26, 27 of the frontal support bend back into their initial positions; the hydraulic damper 11 is moved back in the direction of its initial position. The front, lower end of the frontal support 25, 26, 27 then rests on the base spring 23 over the buffer element 30 with an interposition of the torsion element 28. In the case of further rollover movement, an increasing load is applied to the forefoot region 231. The leaf spring elements 25, 26, 27 bend further, and so the curvature is increased. The torsion element 28, the leaf spring elements 25, 26, 27 and the base spring 23 then interact, wherein the base spring 23 and the torsion element 28 as a leaf spring are connected in parallel. As a result of only being clamped at one end, the torsion element 28 can be displaced along the surface of the base spring 23 when the latter is bent. The frontal support can consist of a leaf spring package made of leaf spring elements 25, 26, 27 or of a single leaf spring element. Torsion about a vertical axis 250 is possible as a result of the structural design of both the support of the hydraulic damper 11 and of the frontal support 25, 26, 27.

Figure 4:
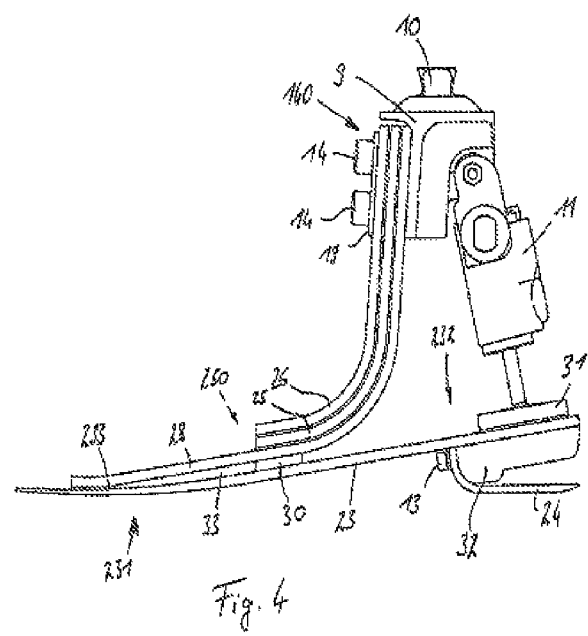
FIG. 4 shows a side view of a variant.

FIG. 4 illustrates a variant of the invention in a side view. The basic design corresponds to the one in accordance with FIG. 2; instead of a torsion element 28 affixed in the heel region 332 of the base spring 23, said torsion element is secured on the base spring in the forefoot region 231 in this variant. The torsion element 28 is secured on the base spring 23 directly after the toe region thereof; in the illustrated exemplary embodiment, this is brought about by an adhesive point 233 or a weld or any other method for securing the torsion element 28 on the base spring 23. A clear space 33 is formed between the attachment point 233 and the buffer element 30, said buffer element 30 enabling a twisting movement of the torsion element 28 relative to the base spring 23. The torsion element 28 extends from the attachment point 233 and after a slight widening of the clear space 33 substantially parallel to the base spring 23, past the buffer element 30 and from there in an arc, which opens into a straight line, to the proximal adapter 9, where it is affixed on the upper end 140 of the frontal support 25, 26 by means of the screws 14. The frontal support 25, 26 is configured as an arrangement of leaf springs extending substantially in parallel; the profile of the frontal support 25, 26 substantially corresponds to the profile of the torsion element 28 in the direction of the proximal adapter 9 from the buffer element 30 onward. Clear spaces for enabling bending and a relative movement of the leaf springs 26, 26, 28 with respect to one another during walking or standing are respectively formed between the frontal support 25, 26 and the torsion element 28.

The buffer element 30 is affixed either to the base spring 23 or to the torsion element 28, such that if the heel is set down hard and the torsion element 28 bends, the latter can move away from the base spring 23 in a relative fashion.

The front end 250 of the frontal support 25, 26 ends approximately level with the buffer element 30 between the torsion element 28 and the base spring 23.

Figure 5:
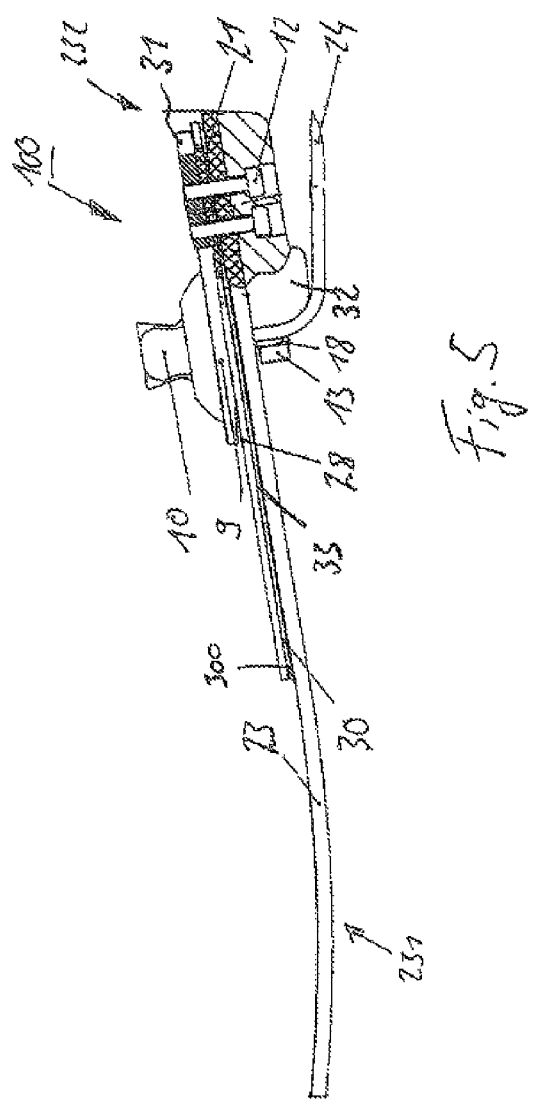
FIG. 5 shows a variant of the prosthetic foot without frontal support.

FIG. 5 illustrates a variant of the invention without frontal support. Analogously to FIGS. 1 and 2, the prosthetic foot has a forefoot region 231 and a heel region 232. The base spring 23 is also made of a fiber composite material in this case, and the explanations in respect of the base spring 23 and the torsion element 28 arranged above the base spring 23 apply correspondingly. A clear space 33 is arranged between the torsion element 28 and the upper side of the base spring 23. A cushioning element 300 for preventing disturbing noises in the case of a relative movement between the torsion element 28 and the base spring 23 can be arranged at the front end of the torsion element 28.

At its rear end, the torsion element 28 is secured at one end to the rear end of the base spring 23 in the heel region 232 by means of the screws 12. Attachment occurs exclusively in the heel region 232 of the base spring 23. The connection apparatus of proximal adapter 9 and adjustment core 10 is, in the walking direction, arranged in front of the attachment elements 12 on the torsion element 30 and optionally has a wedge placed therebeneath in order to simplify the setting of a tilt and thereby simplify an adjustment of the alignment of upper prosthesis components. By directly linking the connection apparatus to the torsion element 28 and the one-ended mount thereof, the upper connection means (not illustrated) can also be displaced or tilted about the longitudinal axis of the foot, in addition to a parallel collection of the torsion element 28 with the base spring 23. The torsion element 28 can likewise serve as an additional spring and bring about a parallel connection between the base spring 23 and the torsion element 28.

The invention claimed is:

1. A prosthetic foot, comprising:
    a base spring having a forefoot region and a heel region;
    a heel spring arranged on the base spring;
    a damping element arranged between the base spring and the heel spring;
    a connection apparatus arranged above the base spring and configured to connect the prosthetic foot to a prosthesis;
    a torsion element;
    a frontal support having an upper end connected to the connection apparatus and a lower end secured to the torsion element;
    wherein the torsion element is configured to twist about the prosthetic-foot longitudinal axis, and is configured as a leaf spring apparatus that is secured at only one end to the base spring, either in the heel region or in the forefoot region, and the lower end of the frontal support having a free end, which terminates at a support area positioned approximately in a center of a length of the base spring;
    wherein during normal use of the prosthetic foot, a free end of the torsion element contacts the base spring at least when the forefoot region is set down in contact with a support surface and during roll over to provide force transmission from the base spring to the frontal support.

2. A prosthetic foot, comprising;
    a base spring with a forefoot region and a heel region;
    a connection apparatus, arranged above the base spring, for affixing the prosthetic foot to a prosthesis;
    a frontal support;
    a torsion element;
    a heel spring is arranged on the base spring;
    a damping element is arranged between the base spring and the heel spring;
    wherein the connection apparatus is secured to the torsion element with the frontal support, the torsion element being configured to twist about the prosthetic-foot longitudinal axis, which torsion element is configured as a leaf spring apparatus, secured at one end to the base spring in the heel region, and a lower end of the frontal support having a free end, which terminates at a support area positioned approximately in a center of a length of the base spring;

wherein during normal use of the prosthetic foot, a free end of the torsion element contacts the base spring at least when the forefoot region is set down in contact with a support surface and during roll over to provide force transmission from the base spring to the frontal support.

3. The prosthetic foot as claimed in 2, wherein the torsion element can be twisted about a medial/lateral axis.

4. The prosthetic foot as claimed in claim 1, wherein a clear space is formed between the base spring and the torsion element.

5. The prosthetic foot as claimed in claim 1, wherein the torsion element can be twisted about a medial/lateral axis.

6. The prosthetic foot as claimed in claim 1, wherein the frontal support is configured as a spring or spring package.

7. The prosthetic foot as claimed in claim 1, wherein the frontal support is configured in such a way that it can be twisted about a vertical axis.

8. The prosthetic foot as claimed in claim 1, wherein a damping element or a resilient element, which is supported on the base spring or on the torsion element in the heel region of the base spring.

9. The prosthetic foot as claimed in claim 8, wherein the damping element is configured as a fluid damper.

10. The prosthetic foot as claimed in claim 8, wherein the damping element has at least one multi-axially movable joint.

11. The prosthetic foot as claimed in claim 2, wherein a clear space is formed between the base spring and the torsion element.

12. A prosthetic foot, comprising:
a base spring with a forefoot region and a heel region;
a connection apparatus arranged above the base spring and configured to connect the prosthetic foot to a prosthesis;
a torsion element configured to twist about a longitudinal axis of the prosthetic foot and having a leaf spring construction, only one end of the torsion element being connected to either the heel region or the forefoot region of the base spring;
a frontal support having an upper end connected to the connection apparatus and a lower end connected to the torsion element, wherein the lower end of the frontal support having a free end, which terminates at a support area positioned approximately in a center of a length of the base spring;
a damping element or a resilient element, which is supported on the base spring or on the torsion element in the heel region of the base spring, the damping element being configured as a fluid damper;
wherein during normal use of the prosthetic foot, a free end of the torsion element contacts the base spring at least when the forefoot region is set down in contact with a support surface and during roll over to provide force transmission from the base spring to the frontal support.

13. The prosthetic foot as claimed in claim 12, wherein a space is formed between the base spring and the torsion element.

14. The prosthetic foot as claimed in claim 12, wherein the torsion element can be twisted about a medial/lateral axis.

15. A prosthetic foot, comprising:
a base spring having a forefoot region and a heel region;
a heel spring arranged on the base spring;
a damping element arranged between the base spring and the heel spring;
a connection apparatus arranged above the base spring and configured to connect the prosthetic foot to a prosthesis;
a torsion element;
a frontal support having an upper end connected to the connection apparatus and a lower end secured to the torsion element;
a damping element or a resilient element, which is supported on the base spring or on the torsion element in the heel region of the base spring, the damping element having at least one multi-axially movable joint;
wherein the torsion element is configured to twist about the prosthetic-foot longitudinal axis, and is configured as a leaf spring apparatus that is secured at only one end to the base spring, either in the heel region or in the forefoot region, and the lower end of the frontal support having a free end, which terminates at a support area positioned approximately in a center of a length of the base spring;
wherein during normal use of the prosthetic foot, a free end of the torsion element contacts the base spring at least when the forefoot region is set down in contact with a support surface and during roll over to provide force transmission from the base spring to the frontal support.

16. The prosthetic foot as claimed in claim 15, wherein a space is formed between the base spring and the torsion element.

17. The prosthetic foot as claimed in claim 15, wherein the torsion element can be twisted about a medial/lateral axis.

18. The prosthetic foot as claimed in claim 15, wherein the frontal support is configured as a spring or spring package.

19. The prosthetic foot as claimed in claim 15, wherein the frontal support is configured in such a way that it can be twisted about a vertical axis.

* * * * *